US00PP21776P2

(12) United States Plant Patent
Pronk et al.

(10) Patent No.: US PP21,776 P2
(45) Date of Patent: Mar. 8, 2011

(54) ***HEUCHERA* PLANT NAMED 'BIG TOP BRONZE'**

(50) Latin Name: *Heuchera villosa*
Varietal Denomination: Big Top Bronze

(75) Inventors: Teunis Johannes Pronk, Hoofddorp (NL); Janmark Van Duijn, Noordwijk (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/592,082

(22) Filed: Nov. 19, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner*—June Hwu
(74) *Attorney, Agent, or Firm*—Audrey Charles

(57) ABSTRACT

A new and distinct cultivar of *Heuchera* plant named 'Big Top Bronze', characterized by its large orbicular-shaped leaves that emerge a dark browned yellow-green and mature with increased dark yellow-green coloration, large inflorescences; and vigorous, mounded growth habit, is disclosed.

1 Drawing Sheet

Latin name of genus and species of plant claimed: *Heuchera villosa.*

Variety denomination: 'Big Top Bronze'.

BACKGROUND OF THE INVENTION

The present invention relates to a new and distinct cultivar of *Heuchera* plant botanically known as *Heuchera villosa* and hereinafter referred to by the cultivar name 'Big Top Bronze'.

The new *Heuchera* cultivar is a polyploid of *Heuchera* 'Brownies', not patented. The polyploidy was induced under laboratory conditions using a colchicine treatment on in vitro plants. Plantlets from the treatment were trialed in a controlled environment at Hillegom, The Netherlands. *Heuchera* 'Big Top Bronze' was discovered and selected as a single flowering plant from the population of treated plants during July 2007.

Asexual reproduction of the new cultivar by in vitro propagation since November 2007 at Hillegom, The Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Big Top Bronze' as a new and distinct cultivar of *Heuchera* plant:

1. Large orbicular-shaped leaves that emerge a dark browned yellow-green and mature with increased dark yellow-green coloration;
2. Large inflorescences; and
3. Vigorous, mounded growth habit.

Of the many commercially available *Heuchera* cultivars, the most similar in comparison to the new cultivar is the parent cultivar 'Brownies', not patented. However, in side by side comparisons, plants of the new cultivar differ from plants of 'Brownies' in at least the following characteristics:

1. Plants of the new cultivar have larger leaves than plants of 'Brownies'; and

2. Plants of the new cultivar have larger inflorescences than plants of 'Brownies'.

While the leaf margins of the both the parent and the new cultivar are crenate, it was unexpected to observe that plants of the new cultivar have leaf margins that are more shallowly lobed than those of the parent plant. In addition, it was unexpected that the leaves of the new cultivar are not rugose like those of the parent plant.

In addition, the new cultivar is similar in comparison to 'Big Top Gold' and 'Big Top Burgundy', co-pending U.S. Plant Patent applications. However, in side by side comparisons, plants of the new cultivar differ from plants of 'Big Top Gold' and 'Big Top Burgundy' primarily in foliage color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Big Top Bronze'. The plants were grown in 5 gallon containers for 2 years in a greenhouse located in Hillegom, The Netherlands.

DETAILED BOTANICAL DESCRIPTION

Figure 1:
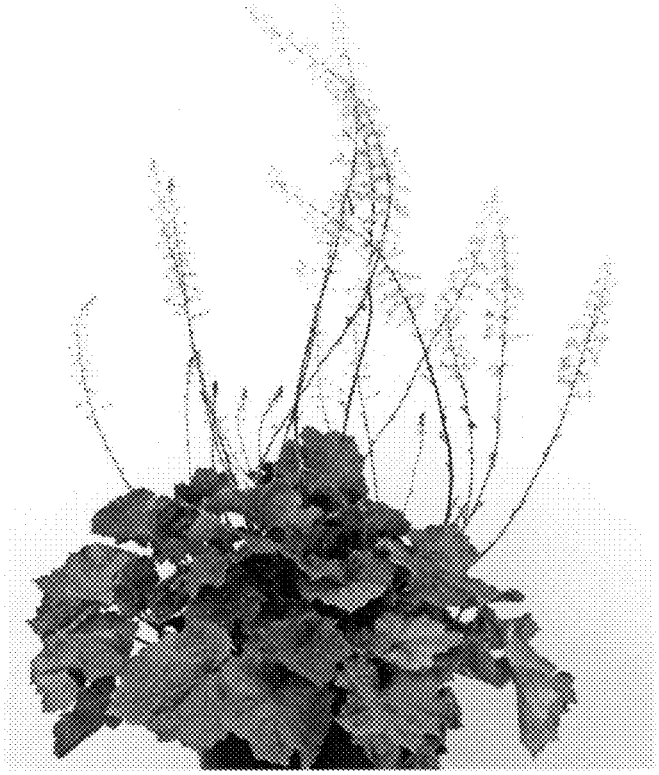
FIG. 1 illustrates a side view of the overall growth and flowering habit of 'Big Top Bronze'.
Figure 2:
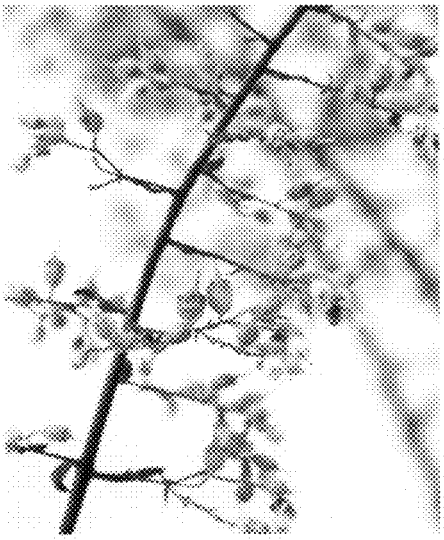
FIG. 2 illustrates a close-up view of an individual inflorescence of 'Big Top Bronze'.
Figure 3:
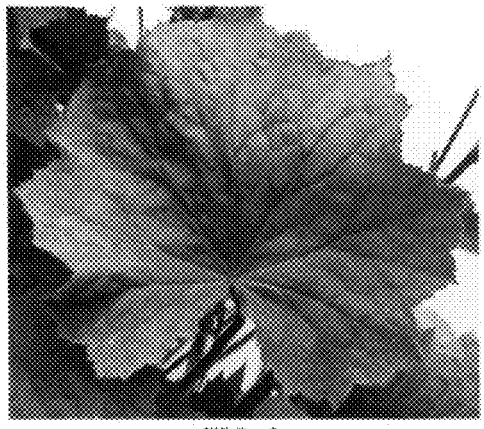
FIG. 3 illustrates a close-up view of the foliage of 'Big Top Bronze'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in August 2009 under natural light conditions in Hillegom, The Netherlands.

The following descriptions and measurements describe plants produced from in vitro propagated plants and grown in 5 gallon containers for 2 years in a plastic-covered greenhouse located in Hillegom, The Netherlands. The plants were grown under conditions comparable to those used in commercial practice having average day temperatures of 18° C. to 25° C. and average night temperatures of 4° C. to 8° C. Measurements and numerical values represent averages of typical plants.

Botanical classification: *Heuchera villosa* cultivar Big Top Bronze.

Parentage:

*Parent.*—*Heuchera* 'Brownies', not patented.

Propagation:

*Type.*—In vitro propagation is preferred, divisions are possible.

*Time to initiate roots in vitro.*—Approximately 10 days at 20° C.

*Time to initiate roots in greenhouse.*—Approximately 20 days at 20° C.

*Time to produce a rooted plantlet in summer.*—Approximately 42 days.

*Root description.*—Fine, fibrous; white to ivory in color.

*Rooting habit.*—Freely branching.

Plant description:

*Commercial crop time.*—Approximately 20 weeks from a rooted tissue culture plantlet to finish in a 1 gallon container.

*Growth habit and general appearance.*—Clump-forming herbaceous perennial, mounded foliage.

*Growth rate.*—Vigorous, approximately 15 cm per month in spring.

*Outdoor plant performance.*—Use as bedding plants or in mixed-container plantings; at least tolerant to temperatures up to 35° C. and hardy to USDA zone 3.

*Size.*—Height from soil level to top of plant plane: Approximately 107.8 cm. Height from soil level to top of foliage: Approximately 42.9 cm. Width: Approximately 113.0 cm.

*Branching habit.*—No branching, basal rosettes of leaves on petioles. Number of rosettes per plant: Approximately 16.

Foliage description:

*General description.*—Moderately durable to environmental stresses. Quantity of leaves per rosette: Approximately 15. Fragrance: None. Form: Simple. Arrangement: Alternate.

*Leaves.*—Aspect: Blade is nearly perpendicular to petiole. Shape: Orbicular. Margin: Crenate, shallowly lobed with an average of 10 lobes per leaf. Apex: Abruptly acute. Base: Hastate, moderately overlapping. Venation pattern: Laciniate. Length of mature leaf: Approximately 17.6 cm. Width of mature leaf: Approximately 18.2 cm. Texture of upper surface: Dull, slightly rough. Sparsely pubescent with short hairs. Texture of lower surface: Slightly glossy, slightly rough. Moderately pubescent with short hairs. Length of pubescence: Approximately 1.5 mm. Color of pubescence: 156D and lighter. Color of upper surface of young foliage: A darkened mixture of 147A and N199A. Color of lower surface of young foliage: Closest to but lighter than N186C. Color of upper surface of mature foliage: 147A with N199A and venation of 146D. Color of lower surface of mature foliage: Closest to but lighter than N186C with venation of 176B to 176C.

*Stipules.*—Two leafy stipules located at the base of each leaf. Apex: Narrow acute. Length: Approximately 1.5 cm. Width: Approximately 2.0 mm. Color: N186C.

*Petiole.*—Length: Approximately 30.7 cm. Diameter: Approximately 5.0 mm. Texture: Moderately pubescent with short hairs. Length of pubescence: Approximately 2.0 mm. Color of pubescence: 156D and lighter. Color of petiole: 176B to 176C.

Flowering description:

*Flowering habit.*—'Big Top Bronze' flowers once a year during late spring to midsummer under outdoor conditions.

*Lastingness of individual flower on the plant.*—Approximately 7 days.

Inflorescence description:

*General description.*—Type: Compound spike emerging from the base of the rosette. Fragrance: None. Length or height including the peduncle: Approximately 101.3 cm. Width: Approximately 10.2 cm. Quantity of flowers per inflorescence: Approximately 450. Quantity of fully open flowers per rosette: Approximately 250. Quantity of flower buds per rosette: Approximately 200.

*Peduncle and rachis.*—Strength: Moderate. Aspect: Approximately 20° angle from vertical. Length: Approximately 99.7 cm. Diameter at midpoint: Approximately 4.0 mm. Texture: Glabrous. Color: 177A to 177B.

Flower description:

*General description.*—Type: Single, campanulate, self-cleaning. Aspect: Drooping to slightly outward.

*Bud.*—Rate of opening: Generally takes 4 days for bud to progress from first color to fully open flower.

*Bud just before opening.*—Shape: Broadly obovate. Length: Approximately 3.0 mm. Diameter: Approximately 2.5 mm. Color: 157D with base of 144B to 144C.

*Corolla.*—Shape: Campanulate. Diameter: Approximately 4.0 mm. Depth: Approximately 6.0 mm.

*Petals.*—Quantity: 5. Arrangement: Rotate. Shape: Narrowly obovate. Appearance: Dull. Margin: Entire. Apex: Acute. Base: Lower half fused into hypanthium. Length: Approximately 3.0 mm. Width: Approximately 0.5 mm. Texture of upper and lower surfaces: Glabrous. Color of upper and lower surface when first open: NN155C. Color of upper and lower surfaces when fully open: NN155C.

*Calyx.*—Shape: Cup. Length: Approximately 4.0 mm. Diameter: Approximately 3.5 mm.

*Sepals.*—Quantity per flower: 5. Shape: Obovate. Appearance: Dull. Margin of free portion: Entire. Apex: Broadly acute. Base: Lower half fused into hypanthium. Length: Approximately 3.0 mm. Width at rim of hypanthium: Approximately 1.5 mm. Texture: Densely pubescent with short hairs. Length of pubescence: Approximately 0.5 mm. Color of pubescence: NN155D. Color of upper and lower surfaces of sepals: 144B to 144C.

*Pedicel.*—Strength: Moderate. Aspect: The pedicel of the central flower of each spikelet is directly on top of the secondary pedicel, pedicels of secondary and tertiary flowers of each spikelet have an average 40° angle from vertical. Length: Approximately 4.0 mm. Diameter: Approximately 0.5 mm. Texture: Glabrous. Color: 177A to 177B.

*Reproductive organs.*—Androecium: Quantity: 5 per flower. Anther shape: Ovate. Anther length: Approximately 1.2 mm. Anther color: 145A to 145B. Filament length: Approximately 3.0 mm. Filament color: N155B to N155C. Pollen amount: Sparse. Pollen color: 22B to 22C. Gynoecium: Pistil quantity: 2 per flower. Pistil length: Approximately 5.0 mm. Stigma shape: Pointed. Stigma color: 157D. Style length: Approximately 4.5 mm. Style color: N155B to N155C. Ovary color: 144C.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Big Top Bronze', substantially as herein shown and described.

* * * * *